(12) United States Patent
Martens et al.

(10) Patent No.: US 9,265,932 B2
(45) Date of Patent: Feb. 23, 2016

(54) METHOD AND SYSTEM FOR DETERMINING SETTINGS FOR DEEP BRAIN STIMULATION

(75) Inventors: Hubert Cécile François Martens, Eindhoven (NL); Michel Marcel Jose Decré, Eindhoven (NL); Kevin Thomas Dolan, Oxford (GB)

(73) Assignee: MEDTRONIC BAKKEN RESEARCH CENTER B.V., Maastricht (NL)

( * ) Notice: Subject to any disclaimer, the term of this patent is extended or adjusted under 35 U.S.C. 154(b) by 294 days.

(21) Appl. No.: 13/575,965

(22) PCT Filed: Feb. 2, 2011

(86) PCT No.: PCT/IB2011/050456
§ 371 (c)(1),
(2), (4) Date: Aug. 17, 2012

(87) PCT Pub. No.: WO2011/098937
PCT Pub. Date: Aug. 18, 2011

(65) Prior Publication Data
US 2012/0303089 A1 Nov. 29, 2012

(30) Foreign Application Priority Data

Feb. 12, 2010 (EP) .................................... 10153466

(51) Int. Cl.
*A61N 1/36* (2006.01)
*A61N 1/05* (2006.01)

(52) U.S. Cl.
CPC .......... *A61N 1/0534* (2013.01); *A61N 1/36082* (2013.01); *A61N 1/36185* (2013.01)

(58) Field of Classification Search
CPC ............ A61N 1/3606; A61N 1/36082; A61N 1/36067; A61N 1/36128

USPC ..................................................... 607/45, 116
See application file for complete search history.

(56) References Cited

U.S. PATENT DOCUMENTS

| 6,366,813 B1 * | 4/2002 | DiLorenzo ...................... 607/45 |
| 2003/0149457 A1 * | 8/2003 | Tcheng et al. .................. 607/48 |

(Continued)

OTHER PUBLICATIONS

International Search Report for PCT/IB2011/050456 dated May 20, 2011.

*Primary Examiner* — Christopher D Koharski
*Assistant Examiner* — Michael D Abreu
(74) *Attorney, Agent, or Firm* — Shumaker & Sieffert, P.A.

(57) ABSTRACT

A method and control system for determining and applying stimulation settings for a brain stimulation probe (10, 12) is provided. The brain stimulation probe (10, 12) comprises a plurality of stimulation electrodes (11). The method comprises for multiple stimulation electrodes (11) of the plurality of stimulation electrodes (11): applying a test current and determining a corresponding patient response, determining a volume of influence based (32, 52, 71, 91) on the test current and a position of the stimulation electrode (11), combining the volume of influence (32, 52, 71, 91) and the corresponding patient response with generalized anatomic knowledge of stimulation induced behavior for associating the volume of influence (32, 52, 71, 91) to an anatomic structure (33, 43, 53), and determining an intersection (41, 51) of the volume of influence (32, 52, 71, 91) and the associated anatomic structure (33, 43, 53). Then, based on the determined intersections (41, 51) an optimal stimulation volume and corresponding stimulation settings for the brain stimulation probe (10, 12) are determined.

6 Claims, 9 Drawing Sheets

(56) References Cited

U.S. PATENT DOCUMENTS

2004/0111127 A1    6/2004  Gliner
2005/0070971 A1*   3/2005  Fowler et al. .................. 607/45
2008/0058773 A1*   3/2008  John .......................... 604/891.1
2008/0215125 A1    9/2008  Farah et al.
2010/0036468 A1    2/2010  Decre et al.

* cited by examiner

METHOD AND SYSTEM FOR DETERMINING SETTINGS FOR DEEP BRAIN STIMULATION

CROSS-REFERENCE TO RELATED APPLICATIONS

This application is a U.S. National Stage of International Patent Application No. PCT/IB2011/050456 filed on Feb. 2, 2011, which claims priority to European Patent Application No. 10153466.7 filed on Feb. 12, 2010, both of which are incorporated herein by reference in their entirety.

FIELD OF THE INVENTION

This invention relates to a method for determining stimulation settings for a brain stimulation probe, the brain stimulation probe comprising a plurality of stimulation electrodes, the method comprising applying a test current to multiple stimulation electrodes and determining corresponding patient responses.

This invention further relates to a computer program product and to a control system for controlling a brain stimulation probe.

BACKGROUND OF THE INVENTION

Deep brain stimulation (DBS) is a surgical treatment involving the implantation of a medical device, which sends electrical pulses to specific parts of the brain. The electrical pulses are delivered to the brain tissue by means of a probe having one or more electrodes, the probe being chronically implanted in the brain. DBS in selected brain regions has provided remarkable therapeutic benefits for otherwise treatment-resistant movement and affective disorders such as chronic pain, Parkinson's disease, tremor, dystonia and obsessive compulsive disorder. During DBS surgery, the most important step in determining the final implant position of a chronic DBS probe is test stimulation. Test stimulation is performed in order to both localize the optimal therapeutic target as well as to investigate the presence of side effect related structures surrounding the target. During test stimulation, a surgical team applies stimulation currents at various positions in and/or around the presumed target area and monitors the patient's response which may, e.g., be improvement (reduction) of disease symptoms and occurrence of (adverse) side effects. In dependence of the observed response, the surgical team configures the position of the probe controlling the stimulation process.

Test stimulation is often applied using an acutely implanted probe carrying a single macroscopic electrode suited for delivery of stimulation currents to the brain tissue. After having configured an optimal position, the acute probe is replaced by the chronic DBS probe. However, test stimulation may be applied also directly using the DBS probe that will be chronically implanted for therapy delivery, which has the advantage that positional errors due to electrode replacement may be avoided.

After a recovery period following the surgical procedure, the optimization of stimulation settings is started. For state-of-the-art chronic DBS probes only four electrodes, spaced apart by e.g. 2, 3, or 4 mm, are available. Currently, the optimization of stimulation settings follows essentially a procedure that is very similar to intra-operative test-stimulation (the procedure described above for the acute probe). To each of the electrodes carried by the chronic probe, stimulation is applied in a sequential order and a neurologist or nurse monitors the patient's response which may, e.g., be improvement (reduction) of disease symptoms and occurrence of (adverse) side effects. In dependence of the observed response, an optimum electrode—or an optimum combination of electrodes—of the chronic probe and stimulation settings are selected. Commonly, the electrode(s) providing lowest threshold for therapeutic effects and a large therapeutic window (i.e. high threshold for adverse-effects in relation to therapeutic threshold) is/are selected.

A preferred chronic DBS probe comprises a plurality of electrodes for providing stimulating electrical pulses at different positions in the target region. For example, the probe may comprise an array of 64 or 128 electrodes. For a simple DBS probe with one or only a few (e.g. four) stimulation electrode(s), the above described test stimulation process may be sufficient for locating the optimum electrode positions (intra-operatively) and/or for obtaining best stimulation settings (post-operatively). A physician or nurse provides one or more test pulses and observes and interprets the patient's physical and/or behavioral responses in order to select the optimum electrode position and/or optimum stimulation settings. However, for a DBS probe with a plurality of stimulation electrodes the known test stimulation process is far less suitable.

The plurality of stimulation electrodes allows accurate positioning of stimulation, e.g. by means of field steering techniques. Stimulation fields induced in the brain tissue and related patient responses are dependent on both the stimulus characteristics delivered to the selected individual electrodes and the resulting interactions between those stimuli. The time needed for testing of a representative number of possible parameter settings and electrode combinations for a DBS probe with a plurality of stimulation electrodes exceeds by far the practical time-frame available for this procedure in a clinical setting.

In view of the above, it is an object of the invention to make the above described determination of stimulation settings for a brain stimulation probe more time efficient.

SUMMARY OF THE INVENTION

According to a first aspect of the invention, this object is achieved by providing a method for determining stimulation settings for a brain stimulation probe, the brain stimulation probe comprising a plurality of stimulation electrodes, the method comprising for multiple stimulation electrodes of the plurality of stimulation electrodes: applying a test current and determining a corresponding patient response, determining a volume of influence based on the test current and a position of the stimulation electrode, combining the volume of influence and the corresponding patient response with generalized anatomic knowledge of stimulation induced behavior for associating the volume of influence to an anatomic structure, and determining an intersection of the volume of influence and the associated anatomic structure. The method further comprises determining an optimal stimulation volume and corresponding stimulation settings for the brain stimulation probe based on the determined intersections.

The patient's response to a stimulus may, e.g., have the form of observable behavior or of less visible physiological changes. Consequently, determining of the responses can both be qualitative assessments by a clinical expert or a nurse such as rigidity, mood, speech as well as quantitative measurements such as accelerometer data or EMG (electromyography) data. The test currents are typically provided as stimulation pulses. Test pulses may either be provided to single electrodes or to groups of electrodes. The volumes of influence for the test pulses depend on several factors such as the stimulation current and the anatomical structure of the tissue surrounding the stimulation electrode.

The volume of influence may be calculated using generalized average electrical properties of brain tissue. The volume of influence is determined relative to the DBS probe, preferably using position data for the stimulation electrode and data describing the actual anatomy and electrical tissue properties of the patient under treatment. It is preferably computed using a realistic conductivity model of the tissue surrounding the probe, but may in practice be approximated using a homogenous conductivity model corresponding to the average conductive properties. For example stereotactic data, neuronavigation data or imaging data, such as CT, MRI or diffusion tensor imaging (DTI) data may be used for determining the patient's anatomy and the position of the stimulation electrode relative to the anatomy. If the patient's anatomy is not known in detail, still the method may work as one may, e.g., simply determine which regions relative to the probe are 'bad' or 'good' for stimulation.

By combining the calculated volume of influence and the corresponding patient response for each tested stimulation electrode or group of stimulation electrodes with generalized anatomic knowledge of stimulation induced behavior, patient responses are associated with specific anatomic structures. Because it is also known which test current, from which (group of) stimulation electrode(s) caused the patient response, it is possible to find out what volumes of influence are overlapping with what neuronal structures. The generalized anatomic knowledge of stimulation induced behavior may, e.g., come from an anatomic atlas with 3D anatomic positions of stimulation induced behavior or from a database comprising relations between anatomic structures and stimulation induced behavior. By making this combination, general knowledge about stimulus induced responses can be used for identifying specific neuronal structures in an individual patient and determining which stimulation electrodes are close to which neuronal structures.

When the intersections of the volumes of influence with the anatomic structures are determined, they are used for determining the optimal stimulation volume. Some observed patient responses will be desirable in view of the treatment of the patient. Other observed patient responses may be undesirable side effects. The optimal stimulation volume is the volume of neuronal tissue close to the probe that should be stimulated for obtaining optimal treatment efficiency with minimal detrimental side-effects. The stimulation volume depends on the stimulation currents that are applied to the different stimulation electrodes and the electric properties of the neuronal tissue close to the stimulation electrodes. When the optimal stimulation volume is known, the corresponding stimulation settings can be derived therefrom.

It is to be noted that it is known to use generalized anatomic knowledge of stimulation induced behavior for detecting brain shift. From 'Detecting brain shift during deep brain stimulation surgery using intra-operative data and functional atlases: a preliminary study', by Pallavaram et al., it is known to compare intra-operative stimulation response data with a functional atlas containing therapeutic response to stimulation data for a population of patients. This comparison is made to determine and correct for intra-operative brain shift. However, the method described in that article is only used for giving a surgeon positional information about specific anatomic structures in order to prevent him from damaging critical structures during an operation. It is not yet known to use generalized anatomic knowledge of stimulation induced behavior for efficiently determining stimulation settings for a multi-electrode brain stimulation probe in the post-operative phase.

According to a second aspect of the invention, a control system is provided for determining stimulation settings for a brain stimulation probe, the brain stimulation probe comprising a plurality of stimulation electrodes, the control system comprising: means for applying test currents to the stimulation electrodes, means for obtaining patient responses corresponding to the applied test currents, and a processor. The processor is arranged for determining volumes of influence based on the test currents and positions of the corresponding stimulation electrodes, for combining the volumes of influence and the corresponding patient responses with generalized anatomic knowledge of stimulation induced behavior for associating the volumes of influence to anatomic structures, for determining intersections of the volumes of influence and the associated anatomic structures, and for determining an optimal stimulation volume and corresponding stimulation settings for the brain stimulation probe based on the determined intersections.

These and other aspects of the invention are apparent from and will be elucidated with reference to the embodiments described hereinafter.

DETAILED DESCRIPTION OF THE INVENTION

Figure 1A:
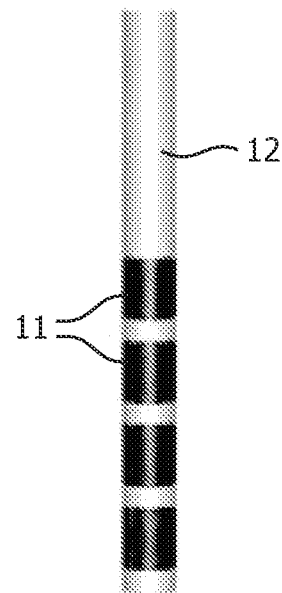
FIGS. 1a and 1b schematically show brain stimulation probes with a plurality of stimulation electrodes, FIG. 2 schematically shows a control system for controlling the brain stimulation probe of FIG. 1.
Figure 1B:
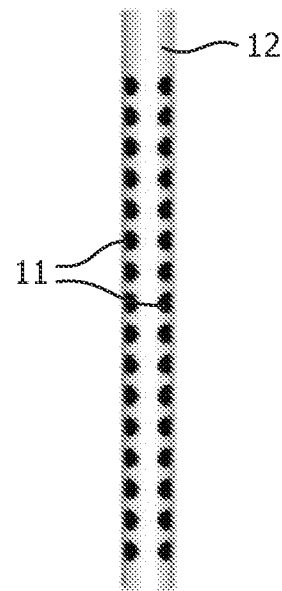

FIGS. 1a and 1b schematically show brain stimulation probes 12, 10 with a plurality of stimulation electrodes 11. The brain stimulation probe 12 of FIG. 1a is a state of the art probe 10 carrying four ring shaped electrodes 11. FIG. 1b shows a preferred DBS probe 10 carrying a multitude of electrodes 11 distributed in a square array. The preferred probe 10 comprises four columns of electrodes 11 for providing stimulation in four different directions (e.g. lateral, anterior, medial and posterior). It is to be noted that this is just a schematic drawing and the actual stimulation probe 10 used may be quite different. What is important for the stimulation probe 10 used in the method and system according to the invention is that it has a plurality of stimulation electrodes 11 distributed over at least part of the probe surface. For example, an array of 64 or 128 electrodes is used.

Figure 2:
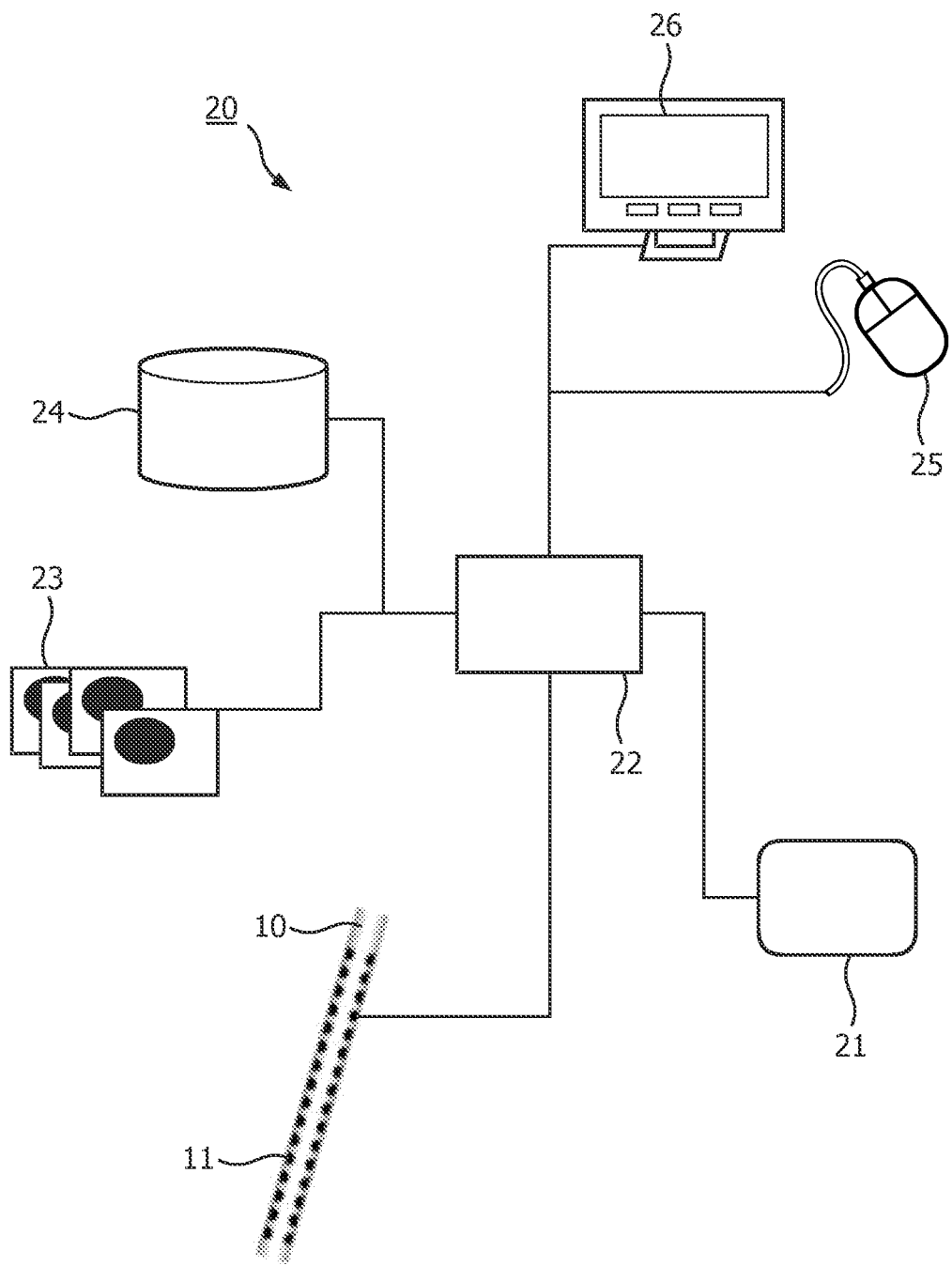

FIG. 2 schematically shows a control system 20 for controlling the brain stimulation probe 10 of FIG. 1. The stimulation probe 10 is coupled to a processor 22. The processor 22 determines and controls the stimulation settings to be applied to the stimulation electrodes 11 for enabling proper functioning of the stimulation probe 10. The processor 22 is preferably also capable of receiving data and signals from the stimulation electrodes 11 in order to obtain information about the functioning of the stimulation probe 10 and its interaction with the environment. The processor 22 is further coupled to a memory 24 for storing, e.g., patient data, software for controlling the system 20 and the generalized anatomic knowledge required for performing the method according to the invention. The control system 20 may be coupled to a local or wide area network (e.g. the Internet) for being able to exchange or share data with other systems.

In use, the probe 10 is implanted in a patient's brain but, preferably, most of the control system 20 is external. The probe 10 may be implanted together with a small control-unit which is arranged for (preferably) wireless communication with the external parts of the control system.

Also coupled to the processor 22 is a display 26 for showing information that may help a user with configuring or using the system 20. For example, the display may show the images 31 of FIGS. 4 to 6. The system 20 may additionally comprise user input means, such as a mouse 25 or other type of pointer device and/or a keyboard. The display 26 may also be used for providing a graphical user interface for enabling a user to configure and control the system 20. For that purpose, the display 26 might have touch screen functionality.

The system 20 may also comprise an input for receiving patient specific anatomical information 23, e.g., in the form of MRI/DTI images or CT scans. The system 20 of FIG. 2 also comprises or is coupled to means 21 for registering patient responses. When stimulation currents are applied to the stimulation electrodes 11, specific neuronal structures may be activated which leads to behavioral or physiological responses. These responses may be registered automatically by the registration equipment 21 or may be reported by an observer, e.g. via the user input means 25. Behavioral and physiological responses may be registered by, e.g., EMG recorders, accelerometers, etc, which are also coupled to the processor 22. The use of the patient specific anatomical information 23 and the registration equipment 21 will further be elucidated below with reference to the flow diagram of FIG. 3.

Figure 3:
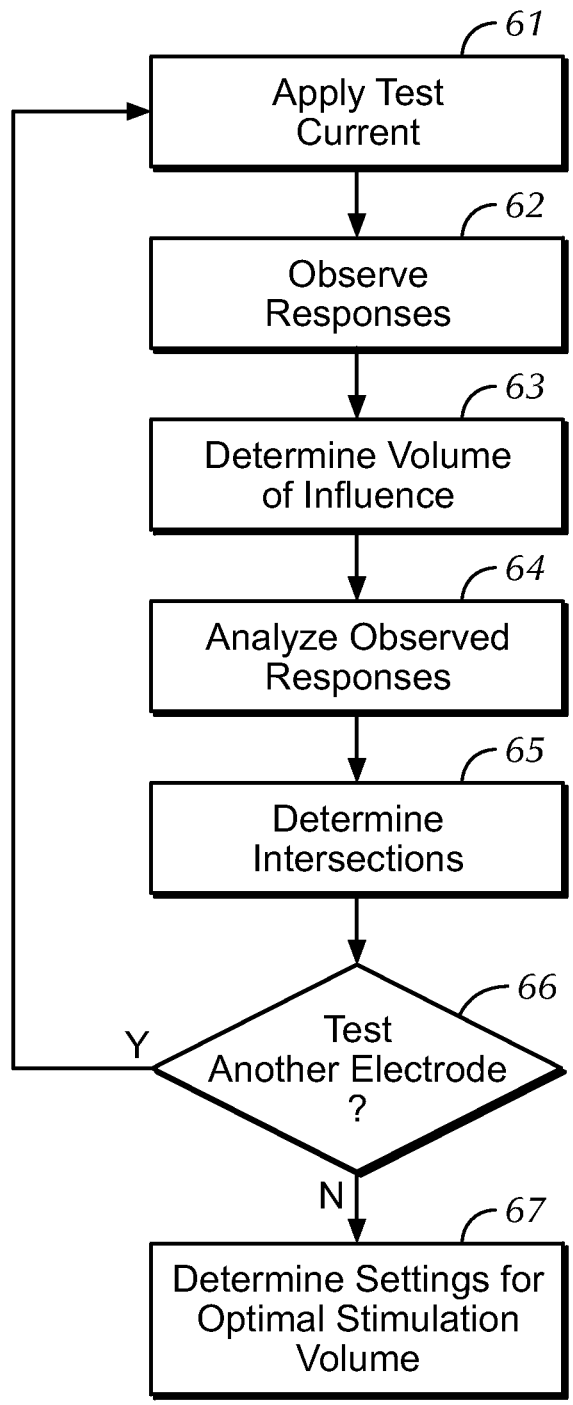
FIG. 3 shows a flow diagram of a method according to the invention.

FIG. 3 shows a flow diagram of a method according to the invention. The purpose of this method is to determine suitable stimulation settings for a stimulation probe 10 as used in the system 20 of FIG. 2. The method may be used either intra-operative, when the probe 10 is to be placed into the brain of a patient to be treated. When used intra-operatively, the method may be used for both finding an optimal position for the probe 10 and for determining suitable stimulation settings. When the method is used post-operatively, i.e. when the position of the probe 10 cannot be changed anymore, the method may be used for determining stimulation settings only. In the following, it is assumed that the method is used post-operatively.

The method starts with stimulus step 61 for applying a test current to at least one of the stimulation electrodes 11. Due to the test pulse, neurons in the brain tissue close to the stimulation electrode 11 are excited. The result of such excitation might lead to changes in behavior or physiology of the patient. These changes may either be positive desired effects such as suppression of tremor or adverse side effects such as involuntary muscle contractions.

In response determining step 62, the responses to a specific test pulse may be observed by, e.g., a doctor or nurse and reported to the system 20 via user input device 25. This reporting may include answering questions, selecting options from a list or filling in response forms. Alternatively, a video camera and/or sound recording means are used for monitoring the patient and video and/or audio recognition software interprets the patient's behavior to determine the response to the test stimulus. Changes in physiology and/or behavior may also be detected by other registration equipment 21, like EMG systems, accelerometers or heart rate monitors.

In influence determining step 63, a volume of influence 32 (see FIGS. 4 and 5) is determined. The volume of influence 32 is the volume of brain tissue in which the applied test current has significant effect. The position of the volume of influence 32 depends on the position of the tested stimulation electrode 11. The dimensions of the volume of influence 32 mainly depend on the amplitude of the test pulse and the electric properties of the brain tissue close to the tested stimulation electrode 11. For determining the volume of influence 32, the processor 22 may use generalized electrical properties for 'average brain tissue'. For more precise calculations, anatomic knowledge (e.g. derived from MRI images) may be used for using different electrical properties for different types of brain tissue. Another way to improve the accuracy of the calculations is to use other stimulation electrodes 11 on the probe 10 to measure electrical properties of the brain tissue close to the tested stimulation electrode 11. In FIG. 6 the influence determining step 63 is performed after determining the patient's response to the stimulus, but it is also possible to do this at an earlier stage.

In response analysis step 64, the observed or registered responses are analyzed to determine what anatomic structures have been stimulated by the test pulse. For this analysis, the processor 22 uses generalized knowledge about expected responses to stimulation of particular anatomic structures. The generalized anatomic knowledge of stimulation induced behavior may, e.g., come from an anatomic atlas with 3D anatomic positions of stimulation induced behavior or from a database comprising relations between anatomic structures and stimulation induced behavior. In addition, information about the volume of influence 32 and/or patient specific anatomic data (e.g. MRI images) may be used to confirm that a specific anatomic structure related to an observed response is indeed within the expected volume of influence 32 of the tested stimulation electrode 11.

In intersection determining step 65, the overlap between the volumes of influence 32 and the anatomic structures giving a response to the test stimulus is determined. As will be shown in FIGS. 5 and 6, the intersections 41 may be visualized in a graphical representation 31 of the probe and/or the surrounding tissue. This step 65 may be limited to only determining the overlap between the volumes of influence and the anatomic structures that lead to detrimental side-effects. Alternative approaches are described below with reference to FIG. 5.

In decision step 66, it is decided whether a further stimulation electrode 11 should be tested. If this is the case, the method goes back to the first step, i.e. stimulus step 61 to provide a test stimulus to the next stimulation electrode 11. Alternatively, the same stimulation electrode is tested repeatedly, but with different test pulses leading to different volumes of influence. Instead of testing single stimulation electrodes 11, the method may also test groups of two or more stimulation electrodes 11 simultaneously.

When all test pulses are provided and all intersections 41 are determined, an optimal stimulation volume can be determined in settings determining step 67. The optimal stimulation volume 52 (visualized in FIG. 6) comprises those parts of the brain that should be stimulated for obtaining efficient treatment with minimal detrimental side-effects. Preferably, the optimal stimulation volume 52 only comprises the target structures and shows no overlap with other structures in the patient's brain. When this is however not possible, the setting should be such that a balance is found between optimal treatment effect and minimal negative side-effects. The optimal stimulation volume 52 corresponds to a particular set of stimulation electrode settings. In this settings determining step 67 the required settings leading to an optimal stimulation volume are determined. The determined setting may be used later for providing the brain stimulation needed for treatment of the patient.

A simple mapping example according to the invention may be as follows: First, the stimulation configuration is chosen such that DBS is provided in a particular (quadrant) direction, e.g. in lateral direction in the middle of the array height (see FIG. 7, FIG. 8). Stimulation is increased and positive effects and adverse effects are monitored. For DBS of the subthalamic nucleus muscle contractions may be provoked by lateral DBS fields with increasing amplitude. A look-up table may be used to determine the most likely orientation (e.g. lateral) of the structure responsible for the side-effects. The threshold for this effect can be translated into an approximate distance of extent of stimulation in that particular direction and this is taken as a boundary beyond which that particular effect may be provoked. This can be repeated for the top and bottom of the array or any other (vertical) positions. Also, the process can be repeated for the other cardinal directions. For example, DBS can be directed preferentially in posterior direction and the threshold for inducing parasthesias may be found. In this way, a 3D shape is 'carved out' around the DBS probe 10 within which there are no/limited side-effects expected. Subsequently, a stimulation setting is configured that leads to optimum overlap of stimulation fields with this carved out volume, and minimal 'spill-over' to areas outside of this.

In a further embodiment of the method according to the invention, again therapeutic effects are monitored. For a given electrode 11 or group of electrodes 11 the threshold(s) for onset of therapeutic effect(s) are determined and clinical improvement is rated, e.g. using clinical rating scales or by means of objective measurements (e.g. accelerometer data). Using a similar mapping procedure as described above, volumes of influence around the probe 10 corresponding to the observed clinical effects are determined and associated to their therapeutic-threshold and therapy-quality measures. A weighting factor dependent on the threshold and therapy quality may be constructed. For example for therapy-rating TR on a scale of 0 to 5 (5 being optimum therapy), a weighting factor TR/IT may be assigned where IT is the threshold intensity for therapeutic effects. A compound therapeutic-effect volume is created by merging the various volumes associated to clinical responses and the individual voxels of this compound volume are given an individual rating that is determined by summing the weighting-factors of individual volumes overlapping that particular voxel. An optimum therapy volume may be determined by selecting a suitable rating-threshold to carve out a sub-volume from the compound volume.

In another embodiment the position of the probe 10 with respect to patient anatomy is e.g. determined by means of a CT scan. The patient anatomy is determined from a (pre-operative) MRI (T1 and T2). An anatomic and functional atlas is registered to the patient. The functional atlas contains information about structures responsible for inducing adverse side-effects. A central selection of the array (e.g. 3 adjacent rings of each 4 electrodes 11 that are centered on the approximate expected target height) is chosen for the delivery of stimulation. Stimulation is started at relatively low amplitude (e.g. <1 mA total stimulus pulse amplitude) and amplitude is gradually increased until a first side-effect is noted for stimulation settings X1. The DBS fields corresponding to this setting X1 is computed. By combining this result with the information from the functional atlas that was registered to the patient MRI, the resulting field-distribution in structure Y1 responsible for this side-effect is determined. For example, maximum or mean field intensity V1 in the structure responsible for the side-effect can be determined. The program then configures a stimulation setting that prevents stimulation fields from exceeding a certain fraction of V1 in this particular structure. In its simplest form this can be achieved by de-activating electrodes 11 close to this region. In more advanced form this can be achieved by means of field steering techniques. Subsequently, total stimulus intensity is further increased (while ensuring that stimulus fields in Y1 do not exceed a specified fraction of V1) until a next side-effect is observed. Structure Y2 responsible for this side-effect is determined and the cross-section of the anatomic position of Y2 with the computed DBS fields is determined. Field intensity V2 (e.g. mean or average) in Y2 is determined, and so forth . . . .

This embodiment may be combined with a Graphical User Interface (GUI) or other device to rate the quality of patient improvements upon DBS administration. When the patient improvement with further increasing amplitude is minimal, the optimization process may be exited.

In an embodiment, the functional brain model is augmented with (or only based on) intra-operatively acquired neuro-electrophysiological data. During intra-operative neuro-electrophysiological examinations a 3D functional mapping of the patient target is performed by means of brain-recordings and test-stimulation. Brain recordings can be assigned to functional/anatomic structures and be registered to patient image data. Brain stimulation effects can be associated to corresponding volumes of interest and also registered to patient anatomy. The resulting 3D functional model can be used in previous embodiments for determining the overlap with volumes of influence when test-stimulation is applied with the chronic DBS-array probe 10.

Figure 4:
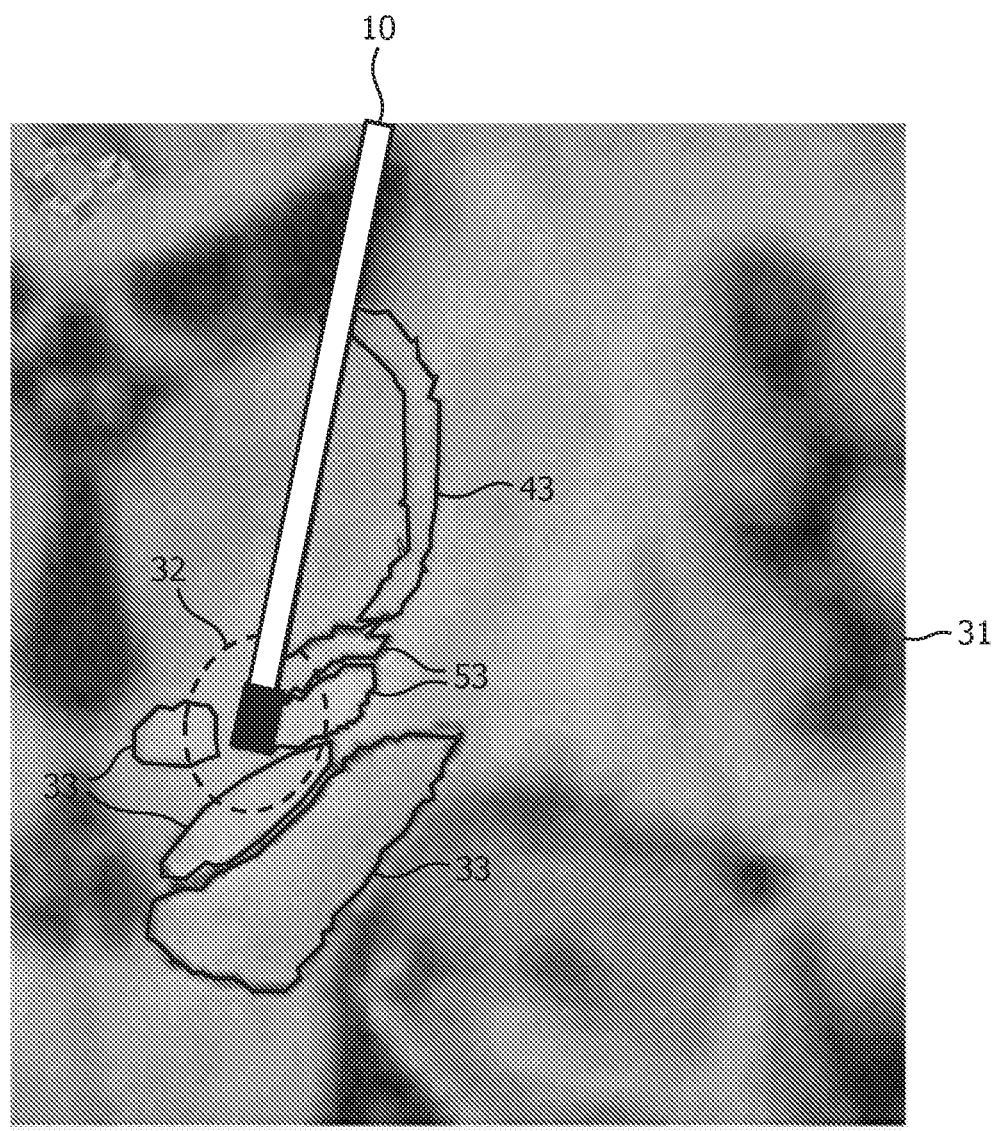
FIG. 4 shows a graphical presentation of a brain probe implanted into a patient's brain.

FIG. 4 shows a graphical presentation 31 of a brain probe 10 implanted into a patient's brain. Such an image 31 may be displayed on the display 26 of the system 20 of FIG. 2 during an operation for implanting and positioning the probe 10 or after such an operation when the preferred optimal settings have to be determined. The image 31 shows an anatomic image of a brain region into which the probe 10 is inserted. Some recognized neuronal structures 33, 43, 53 are highlighted. Additionally, a volume of influence 32 as determined in influence determining step 63 is visualized. The volume of influence 32 shows what parts of the brain will be stimulated when specific settings are applied to specific stimulation electrodes 11. The volume of influence 32 shown may be shown before, during and/or after actually applying the settings to the probe 10.

Figure 5:
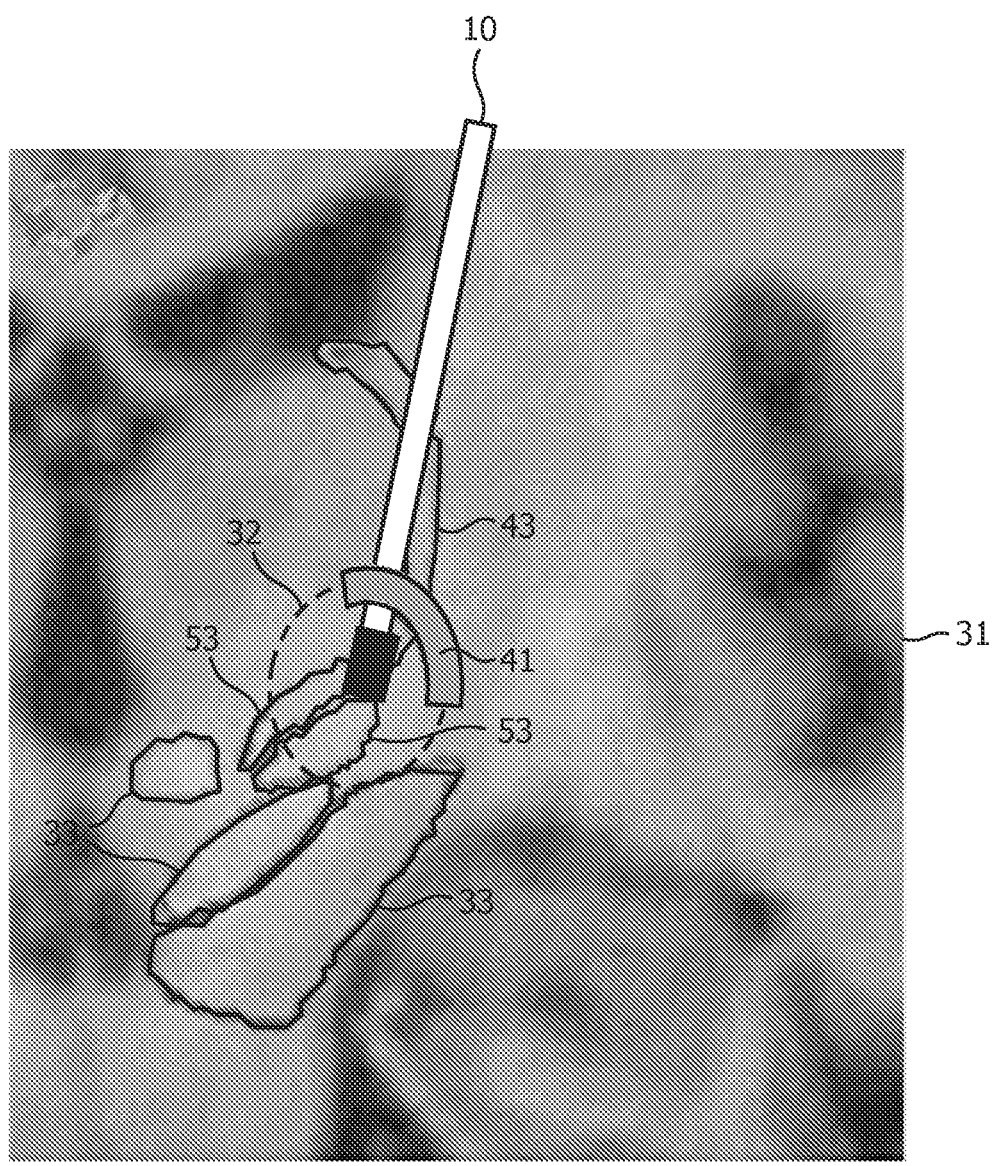
FIG. 5 shows a graphical presentation of an implanted brain probe and an intersection of a volume of influence with a neuronal structure.
Figure 6:
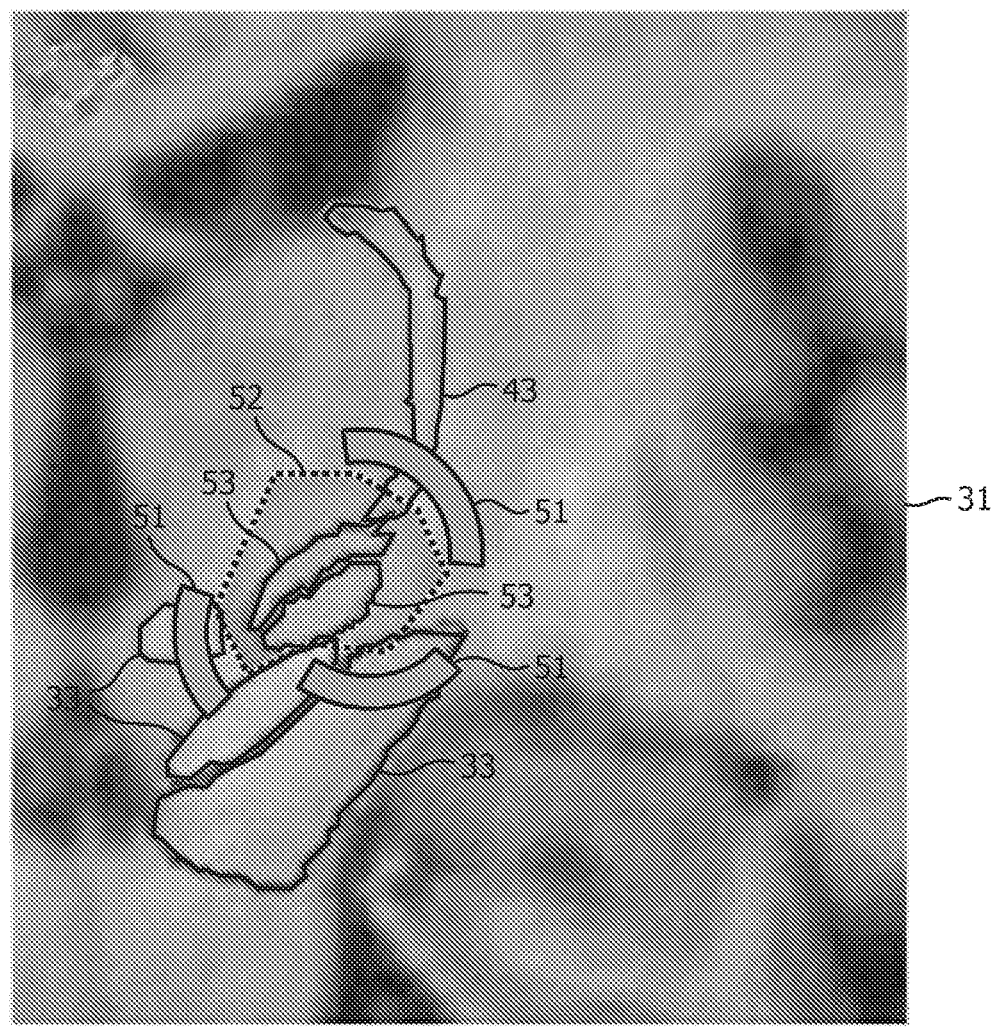
FIG. 6 shows a graphical representation of an optimal stimulation volume as derivable from the method according to the invention, FIGS. 7 and 8 schematically show a volume of influence, and FIG. 9 schematically shows a more complex volume of influence.

FIG. 5 shows a graphical presentation 31 of an implanted brain probe and an intersection 41 of a volume of influence 32 with a neuronal structure 43. Apart from the intersection 41, the image 31 of FIG. 5 shows the similar information as the image 31 of FIG. 4. The intersection 41 shown here indicates that the volume of influence 32 associated with the current settings overlaps with a neuronal structure 43 which causes adverse side-effects when stimulated. In this graphical representation 31, only an intersection 41 indicating overlap with a neuronal structure 43 causing side-effects is shown. Alternatively, also overlap with the neuronal structures 53 to be treated is indicated, possibly using a different color. Color coding may be used for indicating a severity of the expected side-effects. More problematic side-effects may, e.g., be indicated by red intersections 41, while less harmful side-effects are indicated by orange or green intersections 41.

FIG. 6 shows a graphical representation of an optimal stimulation volume 52 as derivable from the method according to the invention. In this image 31, the probe 10 is not shown. The system 20 may provide an option for the user to choose the probe 10 to be or not to be included in the graphical presentation 31 (also for the FIGS. 4 and 5). The optimal stimulation volume 52 is such that it comprises two neuronal structures 53 to be treated, while avoiding as much as possible stimulation of nearby neuronal structures 33, 43 which would result in side-effects. Additionally, this representation 31 also shows the problems that might arise when the probe 10 uses standard stimulation settings instead of the stimulation settings as derived from the method according to the invention. This is done by showing three intersections 51 of side-effect causing structures 33, 43 with the volume of influence for standard settings (not shown). It is to be noted that the showing of these intersections 51 is entirely optional.

Figure 7:
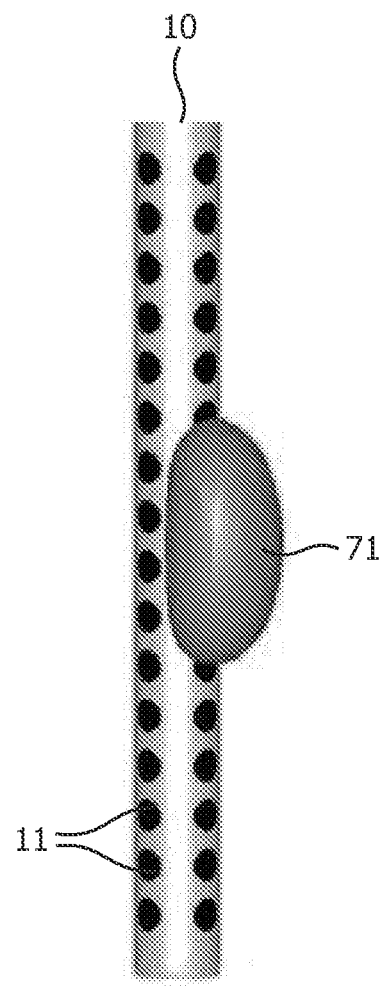
Figure 8:
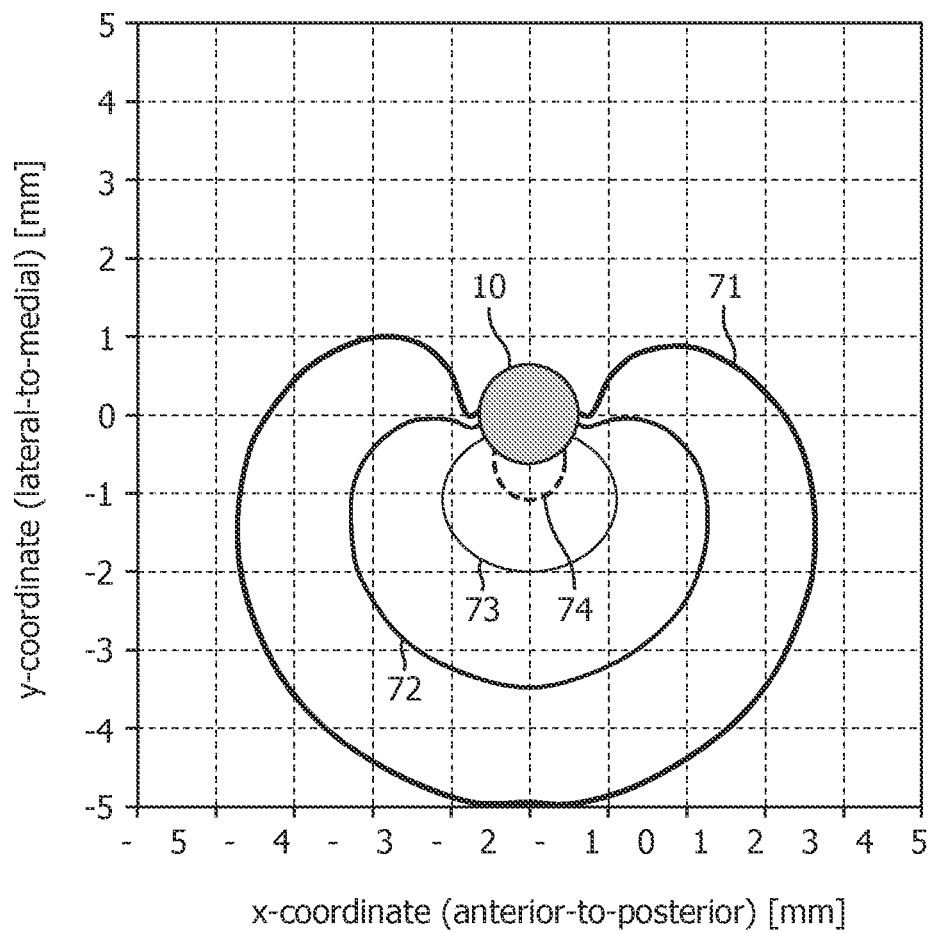

FIGS. 7 and 8 schematically show a volume of influence 71. For this example, a probe 10 similar to the probe 10 in FIG. 1b is used. The stimulation settings are such that a voltage is applied to a group of four electrodes at one side (e.g. lateral) of the probe 10. From these stimulation settings, a volumetric voltage distribution may be computed. The volume of influence 71 indicates at which positions relative to the probe, stimulation of neuronal structures is to be expected.

In FIG. 8, field profiles for directional DBS stimulation into a lateral direction are shown. Stimulation is provided according to the stimulation pattern also shown in FIG. 7. Different stimulus amplitudes lead to different volumes of influence 71, 72, 73, 74. For the profiles in FIG. 8, stimulus amplitude is, e.g., set to 0.5 V (74), 1.0 V (73), 2.0 V (72), 4.0 V (71). With increasing stimulus amplitude, stimulation is provided further away from the probe 10.

Figure 9:
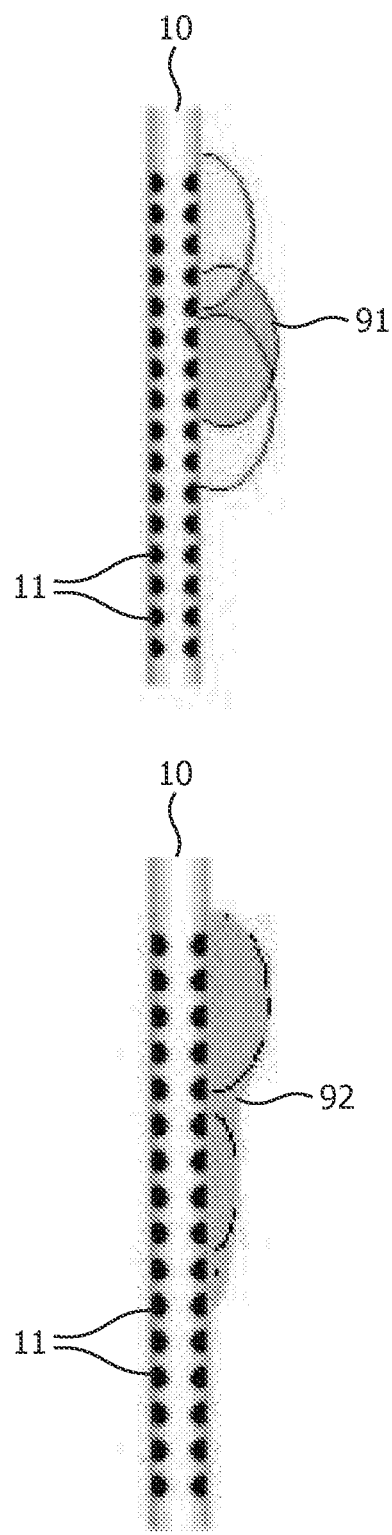

FIG. 9 schematically shows more complex volumes of influence 91, 92. Here, different stimulus amplitudes are applied to different electrodes 11. At some depths, only neuronal structures close to the probe 10 are stimulated (e.g. to avoid adverse side effects). At other depths (e.g. for maximum therapeutic effect), also brain structure further away from the probe 10 are excited.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A control system for determining stimulation settings for a brain stimulation probe, the brain stimulation probe comprising a plurality of stimulation electrodes, the control system comprising:
   means for applying test currents to the stimulation electrodes;
   means for obtaining patient responses corresponding to the applied test currents;
   a database having at least one program comprising relations between anatomic structures and stimulation induced behavior for providing generalized anatomic knowledge of stimulation induced behavior; and
   a processor communicatively coupled to the database, in which the at least one program, when executed by the processor, causes the processor to:
   determine dimensions of respective volumes of influence based on the test currents and positions of the corresponding stimulation electrodes,
   combine the volumes of influence and the corresponding patient responses with the generalized anatomic knowledge of stimulation induced behavior for associating the volumes of influence to anatomic structures, determine intersections of the volumes of influence and the associated anatomic structures, and determine an optimal stimulation volume and corresponding stimulation settings for the brain stimulation probe based on the determined intersections.

2. The control system according to claim 1, further comprising:

registration equipment configured to register patient responses automatically.

3. The control system according to claim 2, wherein the registration equipment is coupled to the processor.

4. The control system according to claim 2, wherein the registration equipment includes EMG recorders and/or accelerometers.

5. The control system according to claim 1, further comprising:

user input means for reporting patient responses to the control system by an observer.

6. The control system according to claim 1, further comprising:

an input configured to receive patient specific anatomical information in the form of MRI/CTI images or CT scans.

* * * * *